(12) United States Patent
Bonin, Jr.

(10) Patent No.: US 8,657,882 B2
(45) Date of Patent: Feb. 25, 2014

(54) EXPANDABLE INTERVERTEBRAL DEVICES AND METHODS OF USE

(75) Inventor: Henry Keith Bonin, Jr., Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1323 days.

(21) Appl. No.: 11/409,708

(22) Filed: Apr. 24, 2006

(65) Prior Publication Data

US 2007/0250171 A1    Oct. 25, 2007

(51) Int. Cl.
*A61F 2/44* (2006.01)

(52) U.S. Cl.
USPC ........................................... 623/17.11

(58) Field of Classification Search
USPC .................. 623/17.11–17.15, 17.16
See application file for complete search history.

(56) References Cited

U.S. PATENT DOCUMENTS

| | | | |
|---|---|---|---|
| 2,424,489 A * | 7/1947 | Moritz | 242/366 |
| 2,536,836 A * | 1/1951 | Bowling | 251/229 |
| 4,553,273 A | 11/1985 | Wu | |
| 4,554,914 A | 11/1985 | Kapp et al. | |
| 4,636,217 A * | 1/1987 | Ogilvie et al. | 623/17.11 |
| 4,657,550 A | 4/1987 | Daher | |
| 4,820,305 A | 4/1989 | Harms et al. | |
| 4,932,975 A | 6/1990 | Main et al. | |
| 5,026,373 A | 6/1991 | Ray et al. | |
| 5,062,850 A | 11/1991 | MacMillian et al. | |
| 5,236,460 A | 8/1993 | Barber | |
| 5,336,223 A | 8/1994 | Rogers | |
| 5,360,430 A | 11/1994 | Lin | |
| 5,397,364 A | 3/1995 | Kozak et al. | |
| 5,480,442 A | 1/1996 | Bertagnoli | |
| 5,522,899 A | 6/1996 | Michelson | |
| 5,571,190 A | 11/1996 | Ulrich et al. | |
| 5,571,192 A | 11/1996 | Schönhöffer | |
| 5,658,335 A | 8/1997 | Allen | |
| 5,702,451 A | 12/1997 | Biedermann et al. | |
| 5,702,453 A | 12/1997 | Rabbe et al. | |
| 5,702,455 A | 12/1997 | Saggar | |
| 5,723,013 A | 3/1998 | Jeanson et al. | |
| 5,725,528 A | 3/1998 | Errico et al. | |
| 5,776,197 A | 7/1998 | Rabbe et al. | |
| 5,776,198 A | 7/1998 | Rabbe et al. | |
| 5,800,550 A * | 9/1998 | Sertich | 623/17.16 |
| 5,989,290 A | 11/1999 | Biedermann et al. | |
| 6,015,436 A | 1/2000 | Schonhoffer | |
| 6,086,613 A | 7/2000 | Camino et al. | |
| 6,156,038 A | 12/2000 | Zucherman et al. | |
| 6,176,881 B1 | 1/2001 | Schär et al. | |

(Continued)

FOREIGN PATENT DOCUMENTS

DE  10357926 B3 *  9/2005
EP  1 080 703 A2  8/2000

(Continued)

*Primary Examiner* — Christian Sevilla

(57) ABSTRACT

The present application is directed to an expandable intervertebral device. One context in which the device may be used is a corpectomy procedure to replace one or more vertebral members. The device is adjustable between a first orientation with a first overall height, and a second orientation with a second overall height. The device generally includes an inner member, an outer member, and a gear. Rotation of the gear causes relative movement between the inner and outer members to move between the first and second orientations and adjust the overall height.

16 Claims, 6 Drawing Sheets

(56) References Cited

U.S. PATENT DOCUMENTS

| | | | |
|---|---|---|---|
| 6,190,413 | B1 | 2/2001 | Sutcliffe |
| 6,190,414 | B1 | 2/2001 | Young et al. |
| 6,193,755 | B1 | 2/2001 | Metz-Stavenhagen et al. |
| 6,193,756 | B1 | 2/2001 | Studer et al. |
| 6,200,348 | B1 | 3/2001 | Biedermann et al. |
| 6,296,665 | B1 | 10/2001 | Strnad et al. |
| 6,299,644 | B1 | 10/2001 | Vanderschot |
| 6,344,057 | B1 | 2/2002 | Rabbe et al. |
| 6,352,556 | B1 | 3/2002 | Kretschmer et al. |
| 6,375,681 | B1 | 4/2002 | Truscott |
| 6,375,683 | B1 | 4/2002 | Crozet et al. |
| 6,395,034 | B1 | 5/2002 | Suddaby |
| 6,409,766 | B1 | 6/2002 | Brett |
| 6,436,140 | B1 * | 8/2002 | Liu et al. .................... 623/17.11 |
| 6,447,547 | B1 | 9/2002 | Michelson |
| 6,454,806 | B1 | 9/2002 | Cohen et al. |
| 6,520,991 | B2 | 2/2003 | Huene |
| 6,524,341 | B2 | 2/2003 | Läng et al. |
| 6,562,074 | B2 | 5/2003 | Gerbec et al. |
| 6,610,090 | B1 | 8/2003 | Böhm et al. |
| 6,616,695 | B1 | 9/2003 | Crozet et al. |
| 6,645,249 | B2 | 11/2003 | Ralph et al. |
| 6,648,917 | B2 | 11/2003 | Gerbec et al. |
| 6,660,038 | B2 | 12/2003 | Boyer, II et al. |
| 6,719,796 | B2 | 4/2004 | Cohen et al. |
| 6,723,126 | B1 | 4/2004 | Berry |
| 6,752,832 | B2 | 6/2004 | Neumann |
| 6,758,862 | B2 | 7/2004 | Berry et al. |
| 6,776,798 | B2 | 8/2004 | Camino et al. |
| 6,783,547 | B2 | 8/2004 | Castro |
| 6,793,678 | B2 | 9/2004 | Hawkins |
| 6,808,538 | B2 | 10/2004 | Paponneau |
| 6,852,129 | B2 | 2/2005 | Gerbec et al. |
| 6,863,673 | B2 | 3/2005 | Gerbec et al. |
| 6,866,682 | B1 | 3/2005 | An et al. |
| 6,908,485 | B2 | 6/2005 | Crozet et al. |
| 2003/0045877 | A1 * | 3/2003 | Yeh ................................ 606/61 |
| 2003/0191531 | A1 | 10/2003 | Berry et al. |
| 2003/0199980 | A1 | 10/2003 | Siedler |
| 2004/0049271 | A1 | 3/2004 | Biedermann et al. |
| 2004/0073314 | A1 | 4/2004 | White et al. |
| 2004/0172129 | A1 | 9/2004 | Schafer et al. |
| 2004/0181283 | A1 | 9/2004 | Boyer, II et al. |
| 2004/0186569 | A1 | 9/2004 | Berry |
| 2005/0004572 | A1 | 1/2005 | Biedermann et al. |
| 2005/0060036 | A1 | 3/2005 | Schultz et al. |
| 2005/0090898 | A1 | 4/2005 | Berry et al. |
| 2005/0113921 | A1 | 5/2005 | An et al. |
| 2006/0241621 | A1 * | 10/2006 | Moskowitz et al. ............ 606/72 |
| 2006/0241762 | A1 * | 10/2006 | Kraus ........................ 623/17.11 |
| 2007/0270960 | A1 * | 11/2007 | Bonin et al. ............... 623/17.11 |

FOREIGN PATENT DOCUMENTS

| | | | |
|---|---|---|---|
| EP | 1 188 424 | A1 | 8/2001 |
| WO | WO 03/073964 | A1 | 9/2003 |
| WO | WO 03/096937 | A1 | 11/2003 |
| WO | WO 2004/026157 | A2 | 4/2004 |
| WO | WO 2004/096103 | A1 | 11/2004 |
| WO | WO 2005/055887 | A2 | 6/2005 |
| WO | WO 2005055887 | A2 * | 6/2005 ................ A61F 2/44 |

* cited by examiner

EXPANDABLE INTERVERTEBRAL DEVICES AND METHODS OF USE

BACKGROUND

The present application is directed to devices and methods for stabilizing vertebral members, and more particularly, to intervertebral implants and methods of use for replacing an intervertebral disc, vertebral member, or combination of both to distract and/or stabilize the spine.

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve. Intervertebral discs are positioned between the vertebral members and permit flexion, extension, lateral bending, and rotation.

Various conditions may lead to damage of the intervertebral discs and/or the vertebral members. The damage may result from a variety of causes including a specific event such as trauma, a degenerative condition, a tumor, or infection. Damage to the intervertebral discs and vertebral members can lead to pain, neurological deficit, and/or loss of motion.

Various procedures include replacing the entirety or a section of a vertebral member, the entirety or a section of an intervertebral disc, or both. One or more replacement implants may be inserted to replace the damaged vertebral members and/or discs. The implants reduce or eliminate the pain and neurological deficit, and increase the range of motion.

SUMMARY

The present application is directed to an intervertebral implant for positioning within the space formed between vertebral members. In one embodiment, the implant includes an inner member and an outer member. A gear is rotatably mounted to the outer member to adjust the relative positioning of the inner and outer members. Bone-engagement features may be positioned on the outer edges of the members to contact the vertebral members and maintain the position of the implant within the intervertebral space.

DETAILED DESCRIPTION

The present application is directed to an expandable intervertebral device. One context in which the device may be used is a corpectomy procedure to replace one or more vertebral members. The device is adjustable between a first orientation with a first overall height, and a second orientation with a second overall height. The device generally includes an inner member, an outer member, and a gear. Rotation of the gear causes relative movement between the inner and outer members to move between the first and second orientations and adjust the overall height.

Figure 1:
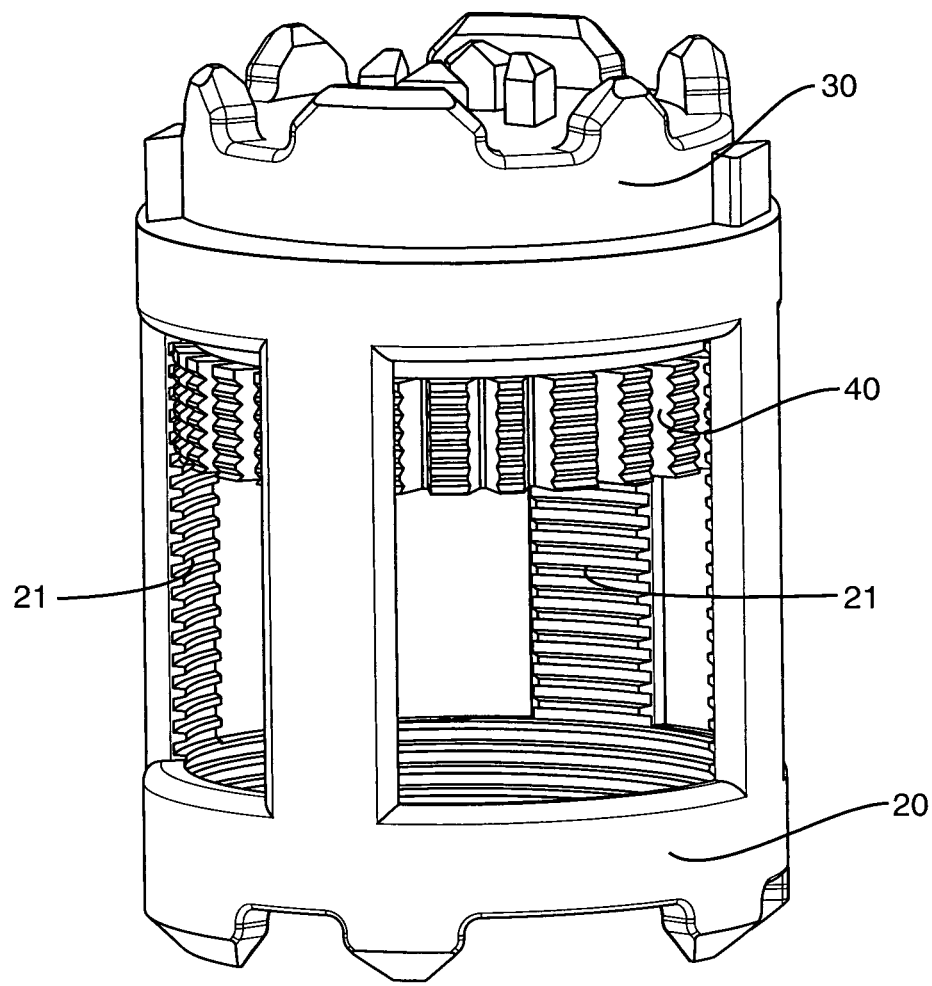
FIG. 1 is a perspective view illustrating a device according to one embodiment.

FIG. 1 illustrates one embodiment of the device and includes an outer member 20, an inner member 30 and a gear 40. The gear 40 is positioned within the outer member 20, and positioned below the inner member 30. Gear 40 is threaded to engage threads 21 on the inner surface of the outer member 20. Rotation of the gear 40 causes the threads to engage, which in turn causes the gear 40 to move axially relative to the outer member 20. This axial movement further causes the inner member 30 to axially move relative to the outer member 20 thereby adjusting the overall height.

Figure 2:
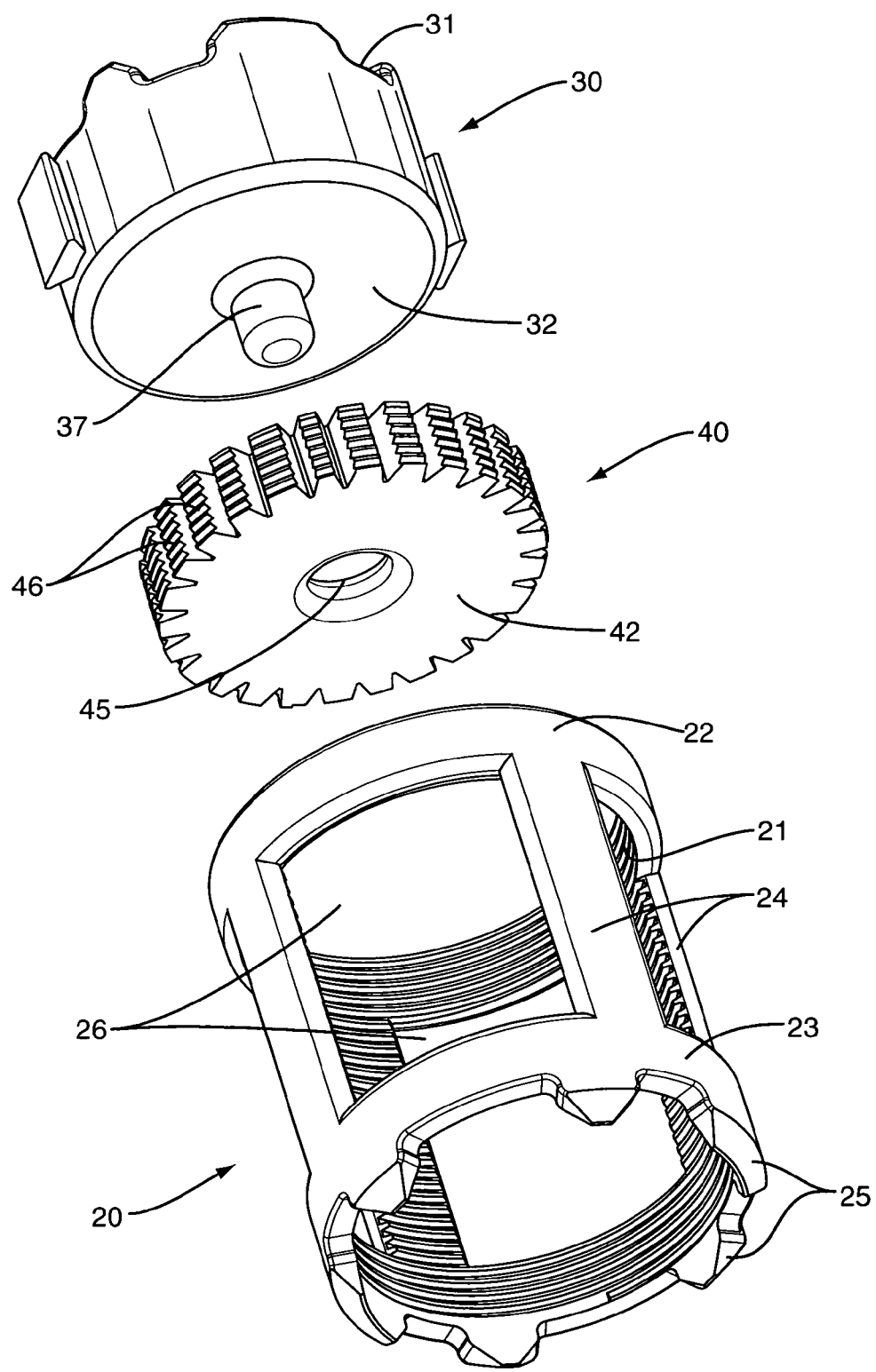
FIG. 2 is an exploded perspective view illustrating a device according to one embodiment.

The outer member 20 contains the inner member 30 and the gear 40. In the embodiments of FIGS. 1 and 2, outer member 20 includes a frame-like structure with a first ring 22 and a second ring 23. Supports 24 connect the rings 22, 23 together and are spaced radially apart with openings 26 positioned therebetween. The outer member 20 may include an overall cylindrical shape with a circular cross-sectional shape. In the embodiments illustrated, the outer member 20 includes a total of two rings 22, 23. In other embodiments, additional intermediate rings (not illustrated) may be positioned within an interior. Likewise, the number of supports 24 may vary depending upon the context of use. One end of the outer member 20 is open to allow the inner member 30 to extend as will be explained below.

The inner surface of the outer member 20 includes threads 21 for engaging the gear 40. The threads 21 may extend the entire height of the outer member 20, or along a limited section. In one embodiment, stops are positioned along the threads 21 at first and second locations to control the extent of movement of the gear 40. In one specific embodiment, a first stop is positioned at the first ring 22, and a second stop is positioned at the second ring 23.

Bone-engagement features 25 extend outward from the second ring 23 to engage a vertebral member. The bone-engagement features 25 may include a variety of shapes and sizes, and may be spaced at a variety of intervals. For instance, the bone-engagement features may be cone-shaped, pyramid-shaped, diamond-shaped, blade-like, or other shapes that may occur to one skilled in the art.

The gear 40 is rotatably positioned within the outer member 20. In one embodiment illustrated in FIGS. 3 and 4, gear 40 includes an upper surface 41 spaced apart from a lower surface 42, and including an outer sidewall 43. The gear 40 may include a substantially circular cross-sectional shape. Threads 44 are positioned along the sidewall 43 to engage the threads 21 on the outer member 20. The threads 44 may extend along an entirety of the sidewall 43 as illustrated, or may extend over a limited section. The thickness of the gear 40 defined between the upper and lower surface 41, 42 may vary.

Figure 3:
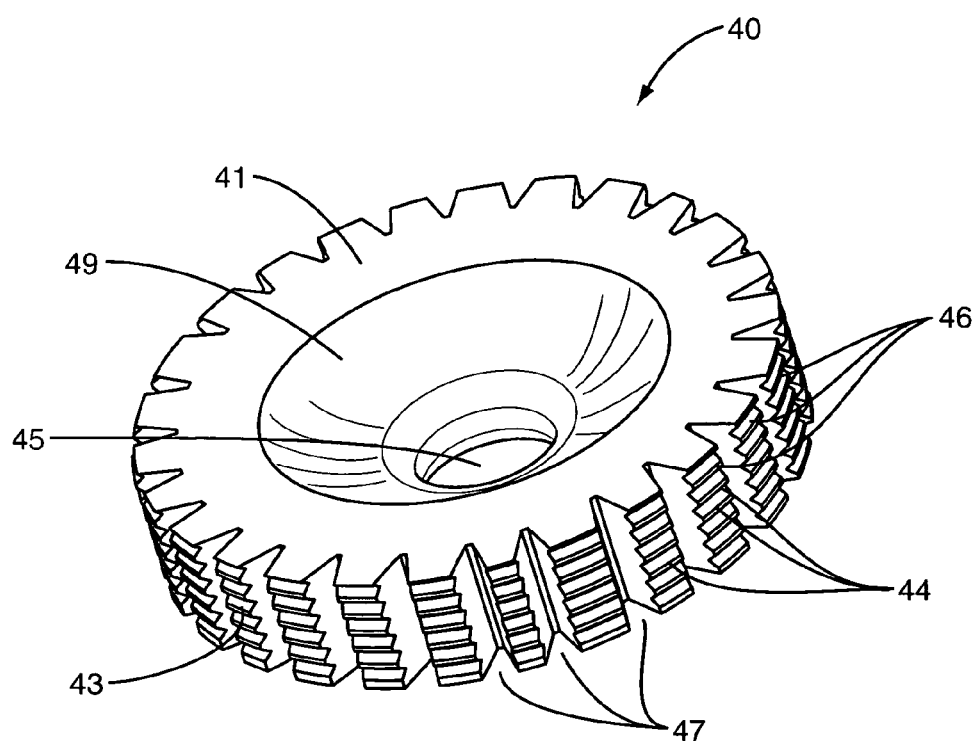
FIG. 3 is a top perspective view illustrating a gear according to one embodiment.
Figure 4:
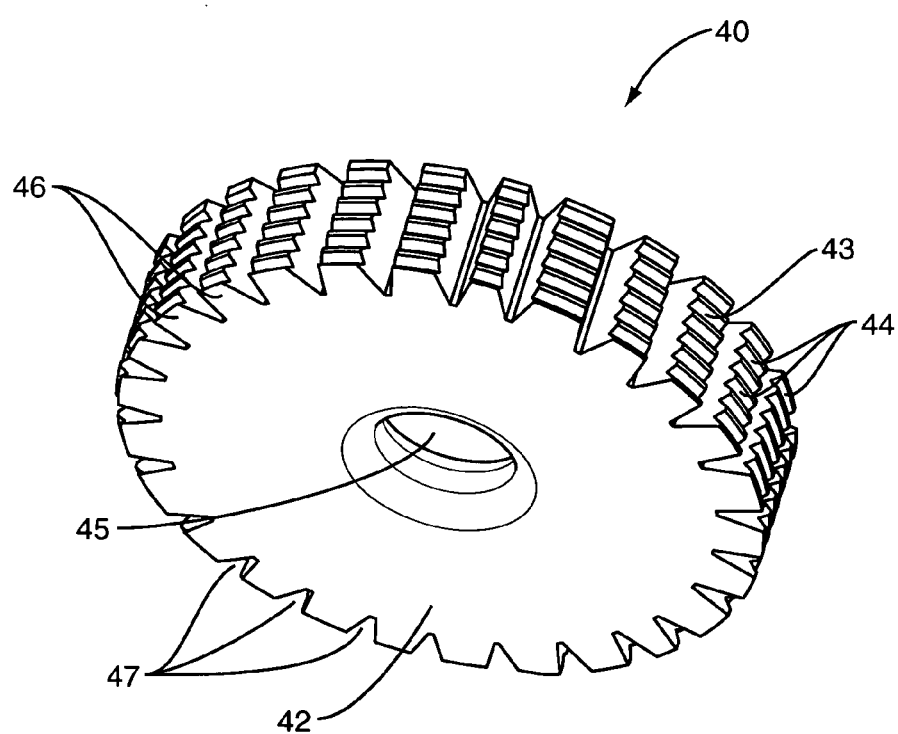
FIG. 4 is a bottom perspective view illustrating a gear according to one embodiment.

An aperture 45 may extend through a center of the gear 40 to position the inner member 30 as will be explained in more detail below. The upper surface 41 may be relatively flat, and may further include a concave section 49. In one embodiment as illustrated in FIG. 3, the concave section 49 is centered about the aperture 45. Concave section 49 may limit the amount of surface area in contact with the inner member 30 during rotation of the gear 40. Concave section 49 may also assist in maintaining the position of the inner member 30 relative to the gear 40.

The sidewall 43 further includes teeth 46 separated by gaps 47. The teeth 46 are evenly spaced about the circumference of the gear 40 to engage a rotational device. In the embodiment illustrated, the gaps 47 form an acute angle at the intersection of first and second surfaces. The gaps 47 may include other shapes and sizes in other embodiments.

Figure 5:
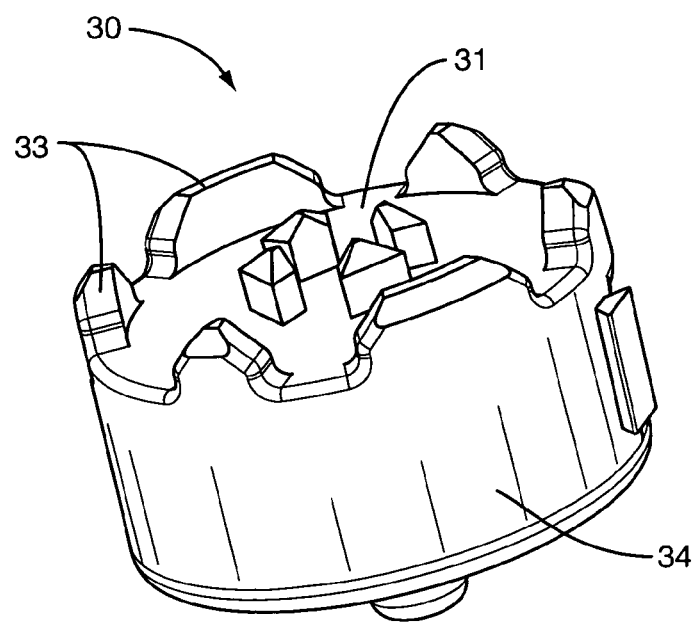
FIG. 5 is a top perspective view illustrating an inner member according to one embodiment.
Figure 6:
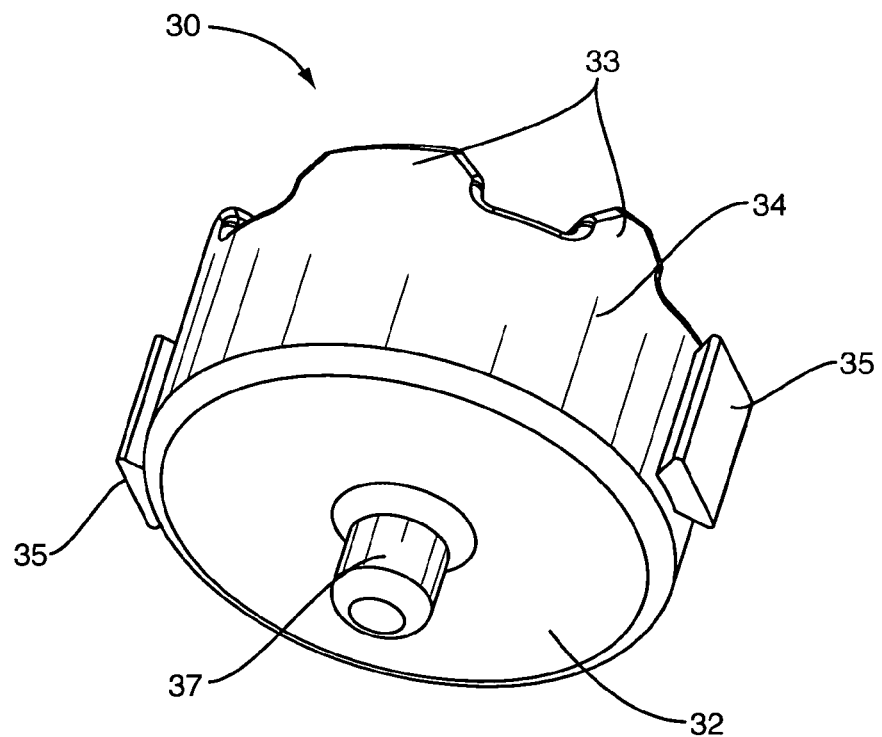
FIG. 6 is a bottom perspective view illustrating an inner member according to one embodiment.

The inner member 30 axially moves relative to the outer member 20 through contact with the gear 40. FIGS. 5 and 6 illustrate embodiments of the inner member 30 that include an upper surface 31 and lower surface 32 spaced apart and including a sidewall 34. The upper surface 31 may include bone-engagement features 33 that engage a vertebral member. The bone-engagement features 33 may be spaced at a variety of locations along the upper surface 31, including the peripheral edge and within an interior section. The bone-engagement features 33 may include a variety of shapes and sizes similar to bone-engagement features 25 on the outer member 20.

The lower surface 32 may include a post 37 that extends outward and is sized to fit within the aperture 45 of the gear 40. Post 37 is positioned at a center of the lower surface 32, and may include a variety of shapes and lengths. The outer edge of the post 37 may be rounded to ease insertion into the aperture 45, and assist in maintaining the post 37 positioned within the aperture 45. The post 37 may include an engagement mechanism, such as outwardly-extending arms, a flared end, or a swivel connection, that positively connects to the gear 40. In one embodiment, the lower surface 32 is substantially flat to decrease frictional contact during rotation of the gear 40.

Figure 11:
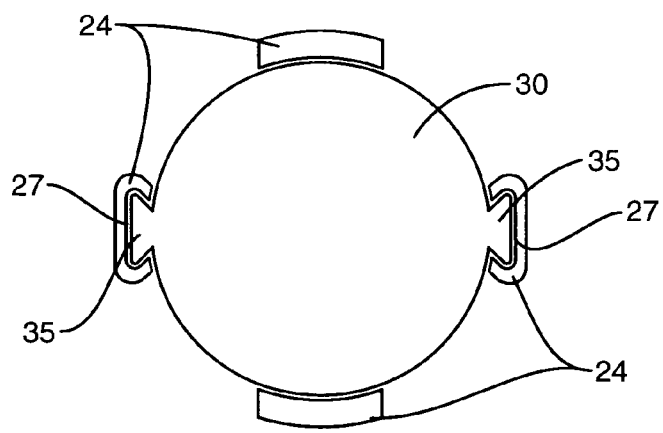
FIG. 11 is a schematic view illustrating an inner member and an outer member according to one embodiment.

One or more ribs 35 may extend along the sidewall 34 and mate with the supports 24 on the outer member 20. In one embodiment as illustrated in FIG. 11, the ribs 35 fit within a track 27 within the supports 24 to maintain the alignment of the inner member 30 relative to the outer member 20. The number of ribs 35 and tracks 27 may vary depending upon the context. The ribs 35 may also engage the outer member 20 to prevent rotation of the inner member 30 during rotation of the gear 40. That is, the ribs 35 help maintain a rotational orientation of the inner member 30 relative to the outer member 20. In one specific embodiment as illustrated in FIG. 11, the ribs 35 include a dovetail shape that corresponds with a similar shape of the track 27 in the supports 24.

Figure 7:
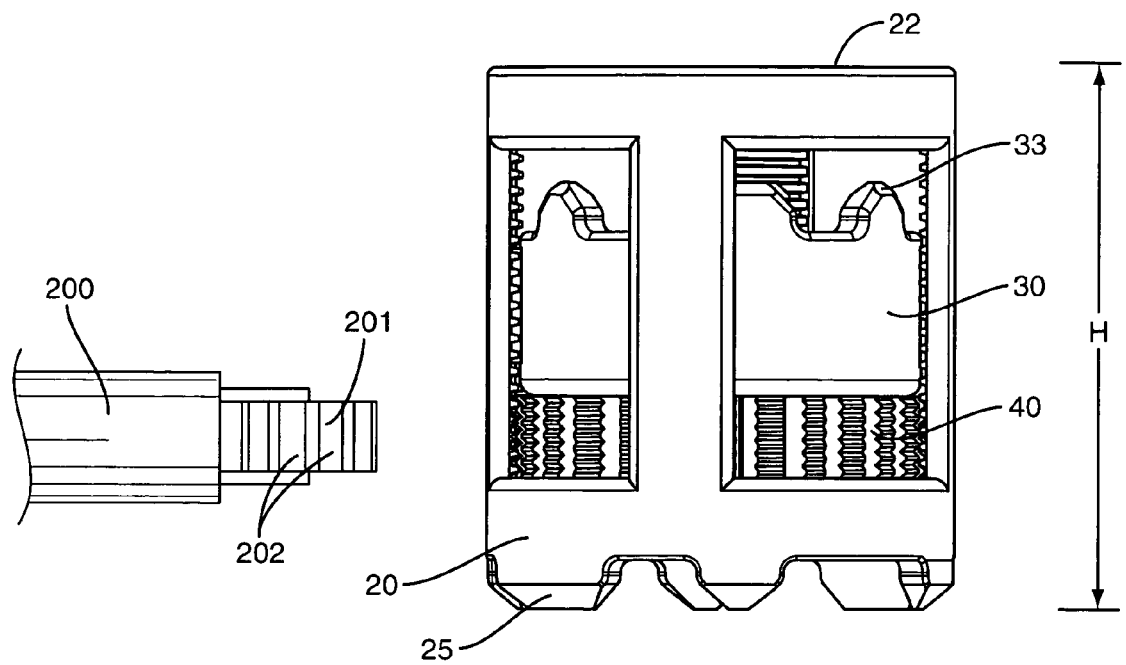
FIG. 7 is a side view illustrating a device and a tool according to one embodiment.
Figure 8:
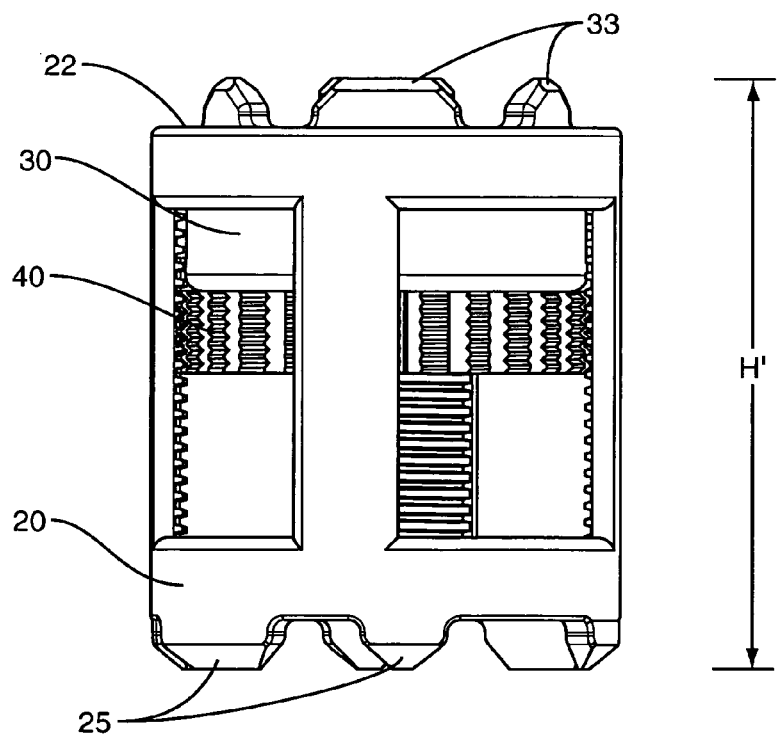
FIG. 8 is a side view illustrating a device according to one embodiment.

FIGS. 7 and 8 illustrate one method of adjusting a height of the device. In an initial orientation as illustrated in FIG. 7, the inner member 30 is positioned within the interior of the outer member 20. The bone-engagement features 33 of the inner member 30 are recessed below the upper edge of the first ring 22 of the outer member 20. The overall height H of the device is the height of the outer member 20 measured from the upper edge of the first ring 22 to the lower tips of the bone-engagement features 25.

When the gear 40 is disposed within the outer member 20, the gear teeth 46 are exposed through the openings 26. A surgeon can engage the gear teeth 46 using a surgical tool 200 with a rotatable gear 201. The rotatable gear 201 includes gear teeth 202 that are sized and spaced to mate with teeth 46 on the gear 40. The surgical tool 200 may include an unillustrated drive train and drive source (e.g., manual, electric, pneumatic) that transmits a rotating force to the gear 201. The gear 201 is brought into contact with the gear 40 with the teeth 202 engaging with teeth 46. Rotation of the gear 201 is transferred to the gear 40 causing it to move upward and downward relative to the outer member 20. The gear 40 will move up or down depending on the direction of rotation and on the direction of the threads. U.S. Pat. No. 6,190,414 discloses a surgical tool for rotation and is herein incorporated by reference.

As the gear 40 moves upward and downward relative to the outer member 20, the gear 40 also moves the inner member 30. The gear 40 may be positively connected to the inner member 30, or may just be positioned against the inner member 30. Rotation of the gear 40 causes the upper surface 41 of the gear 40 to slide across the lower surface 32 of the inner member 30. The inner member 30 moves axially relative to the outer member 20, but does not rotate. Therefore, the bone-engagement features 33 securely purchase within the vertebral member as the overall height of the device increases.

FIG. 8 illustrates the device in an expanded, second orientation. The gear 40 has been moved upward along the outer member 20. This movement has caused the inner member 30 to extend beyond the outer member 20. Specifically, the bone-engagement features 33 of the inner member 30 extend outward beyond the first ring 22 of the outer member 20. The device has an overall height H' in this orientation that is greater than height H illustrated in the orientation of FIG. 7. Additional rotation of the gear 40 may cause the inner member 30 to extend further outward beyond the outer member 20 and further increase the height. The extent of outward movement may be controlled by stops placed along one or both threads 21, 44 on the outer member 20 and gear 40.

Rotation of the gear 40 in the opposite direction will cause the overall height to decrease. The rotation causes the gear 40 and thus the inner member 30 to move downward within the outer member 20.

In one embodiment, the upper surface 41 of the gear 40 directly contacts the lower surface 32 of the inner member 30. In other embodiments, intermediate elements may be positioned between the gear 40 and the inner member 30.

The outer member 20, inner member 30, and gear 40 may include a variety of configurations. In one embodiment, the outer member 20 includes multiple openings 26 to accommodate the tool 200. In another embodiment, the outer member 20 includes a single opening 26.

Figure 9:
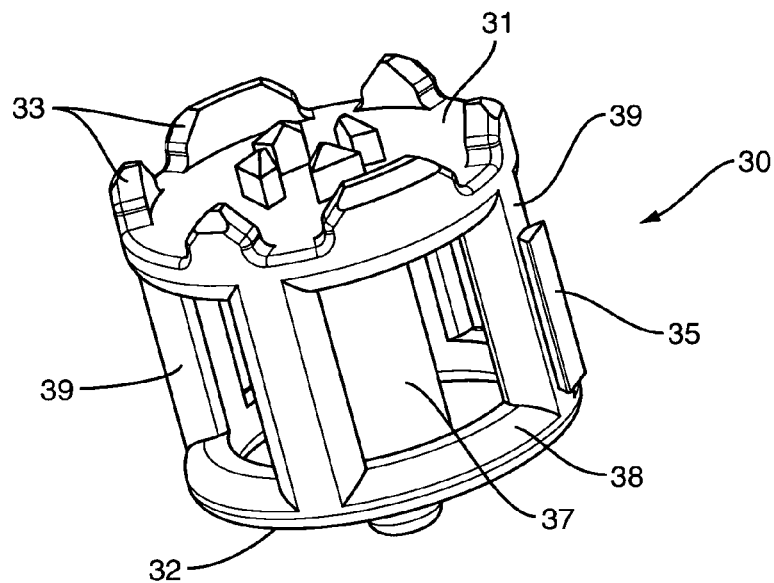
FIG. 9 is a perspective view illustrating an inner member according to one embodiment.

FIG. 9 illustrates another embodiment of the inner member 30. This embodiment features supports 39 that extend between the upper surface 31 and a lower ring 38. The supports may be spaced apart forming a substantially open interior. A post 37 is positioned within the interior and extends downward from the upper surface 31 beyond the lower ring 38 to engage the gear 40 in a manner similar to that described above. The lower ring 38 includes a lower surface 32 that contacts the gear 40. Ribs 35 may be positioned on one or more of the supports to engage the outer member 20 and prevent rotation of the inner member 30.

Figure 10:
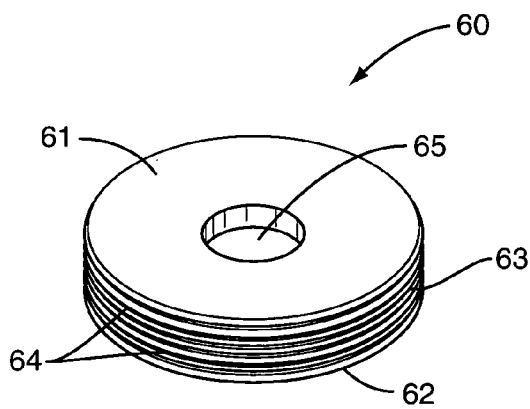
FIG. 10 is a perspective view illustrating a threaded member according to one embodiment.

In the embodiments disclosed above, the gear 40 includes teeth 46 along an outer edge. In another embodiment as illustrated in FIG. 10, a threaded member 60 is sized to fit within the outer member 20. Threaded member 60 includes an upper surface 61, lower surface 62, and a sidewall 63. Threads 64 are position on the sidewall 63 to engage threads 21 on the outer member 20. An aperture 65 may be positioned to receive the post 37 on the inner member 30. Threaded member 60 is similar to gear 40, except there are no teeth positioned along the sidewalls 63. Rotation of the threaded member 60 may be accomplished by manual rotation by the surgeon, or a surgical tool that engages with the member 60 at the upper or lower surfaces 61, 62, or the sidewall 63.

The device may be constructed from a variety of materials including biocompatible metal alloys such as titanium, cobalt-chrome, and stainless steel. Other constructions include non-metallic materials such as ceramics, resins, or polymers, such as UHMWPE and implantable grade polyetheretherketone (PEEK) or other similar materials (e.g., PAEK, PEKK, and PEK). The device may also be constructed of synthetic or natural bone or bone composites. Those skilled in the art will comprehend that there are a variety of other suitable material choices.

The device may be used in a variety of different vertebral procedures. The device may be inserted using different approaches, including anterior, posterior, postero-lateral, antero-lateral and lateral. Further, the device may be used in various regions of the spine including the cervical, thoracic, lumbar and/or sacral portions of the spine.

Spatially relative terms such as "under", "below", "lower", "over", "upper", "inner", "outer", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. An intervertebral implant to be positioned within a space formed between vertebral members, the implant comprising:
    an outer member including sidewalls that form an interior space extending along and centered about a longitudinal axis of the outer member, the sidewalls including threads along an inner surface;
    an inner member including a first surface, and an opposing second surface with the second surface extending across the interior space such that the longitudinal axis extends through the second surface, the inner member also including a lateral sidewall that extends between the first and second surfaces, the inner member being sized to fit within the interior space, the inner member including a post that extends outward from the second surface with the longitudinal axis extending through the post; and
    a threaded member sized to fit within the interior space and positioned in contact with the second surface of the inner member, the threaded member being threaded along an outer peripheral wall to engage with the threads along the inner surface of the outer member, the threaded member including an aperture that receives the post;
    the threaded member and the inner member each being movable along the longitudinal axis between a first position with the first surface of the inner member being positioned within the outer member and a second position with the first surface of the inner member extending outward from the outer member to contact one of the vertebral members.

2. The implant of claim 1, wherein an overall height of the implant is greater in the second position than in the first position.

3. The implant of claim 1, wherein the sidewalls of the outer member include at least one opening that leads into the interior space.

4. The implant of claim 1, wherein the outer member is substantially cylindrical with an open end through which the inner member extends outward from in the second position.

5. The implant of claim 4, wherein the first surface of the inner member and a second end of the outer member each include a bone engagement feature configured to contact the vertebral members.

6. The implant of claim 1, wherein the threaded member further comprises a concave section that limits an amount of surface contact between the second surface of the inner member and the threaded member.

7. The implant of claim 1, wherein the threaded member further includes teeth spaced apart at intervals along the outer peripheral wall.

8. The implant of claim 1, wherein the inner member further includes at least one rib that extends radially outward from the lateral sidewall that contacts the outer member to prevent rotation of the inner member during movement between the first position and the second position.

9. The implant of claim 1, wherein the inner member comprises a substantially open interior section.

10. An intervertebral implant to be positioned within a space formed between vertebral members, the implant comprising:
    an outer member including a longitudinal axis and further including sidewalls that form an interior space, the sidewalls including threads along an inner surface;
    an inner member sized to fit within the interior space and including a first surface and a second surface, the second surface extending across the interior space and having a post with the longitudinal axis extending through the post; and
    a threaded member sized to fit within the interior space and being threaded along an outer peripheral wall to engage with the threads along the inner surface of the outer member, the threaded member further including an engagement surface that extends across the interior space and faces towards and contacts against the second surface of the inner member, the engagement surface including a recess to limit an amount of contact area with the inner member;
    rotation of the threaded member causes movement of the threaded member and the inner member along the longitudinal axis of the outer member to increase an overall height of the implant and position the inner member in contact with one of the vertebral members, the inner member being configured to prevent rotation during rotation of the threaded member.

11. The implant of claim 10, wherein the threaded member is operatively coupled to the inner member.

12. The implant of claim 10, wherein the inner member further includes at least one rib that extends radially outward beyond an exterior sidewall of the inner member and that fits within a groove that extends along a longitudinal height of the outer member to prevent rotation of the inner member during rotation of the threaded member.

13. The implant of claim 10, wherein the inner member is movable along the longitudinal axis between a first position with a first edge of the inner member positioned within the interior space below an axial end of the outer member and a second position with the first edge extending outward from the interior space above the axial end of the outer member.

14. The implant of claim 13, further comprising bone-engagement features positioned on the inner member and the outer member to engage the vertebral members in the second position.

15. The implant of claim 10, wherein the post is spaced away from the first surface of the inner member.

16. The implant of claim 10, wherein the threaded member further includes teeth that extend inward from the outer peripheral wall and are spaced apart at intervals along the outer peripheral wall.

* * * * *